(12) United States Patent
Lee et al.

(10) Patent No.: US 8,450,330 B2
(45) Date of Patent: May 28, 2013

(54) PHARMACEUTICAL ACCEPTABLE COMPOSITION CONTAINING NON-STEROIDAL ANTI-INFLAMMATORY DRUG AND LOCAL ANESTHETICS

(75) Inventors: Fangchen Lee, Taichung (TW); Hui-Ling Shieh, Taichung (TW); Chiung-Ju Tsai, Taichung (TW); Shin-Hong Jang, Taichung (TW)

(73) Assignee: Yung Shin Pharmaceutical Industrial Co., Ltd., Taichung (TW)

( * ) Notice: Subject to any disclaimer, the term of this patent is extended or adjusted under 35 U.S.C. 154(b) by 386 days.

(21) Appl. No.: 12/199,849

(22) Filed: Aug. 28, 2008

(65) Prior Publication Data

US 2009/0062315 A1 Mar. 5, 2009

Related U.S. Application Data

(60) Provisional application No. 60/968,654, filed on Aug. 29, 2007.

(51) Int. Cl.
*A01N 43/90* (2006.01)
*A01N 37/30* (2006.01)
*A61K 31/52* (2006.01)
*A61K 31/205* (2006.01)

(52) U.S. Cl.
USPC ........................................ 514/263.1; 514/554

(58) Field of Classification Search
None
See application file for complete search history.

(56) References Cited

U.S. PATENT DOCUMENTS

| 3,968,205 | A | | 7/1976 | Bickel | |
|---|---|---|---|---|---|
| 4,211,771 | A | * | 7/1980 | Witkowski et al. | 514/43 |
| 5,534,242 | A | | 7/1996 | Henry | |
| RE37,727 | E | | 6/2002 | Hind | |
| 2004/0067211 | A1 | * | 4/2004 | Bamba | 424/70.12 |
| 2004/0068007 | A1 | * | 4/2004 | Lee et al. | 514/554 |
| 2004/0161437 | A1 | * | 8/2004 | Bleckmann et al. | 424/401 |
| 2004/0180066 | A1 | * | 9/2004 | Lee et al. | 424/400 |
| 2004/0200954 | A1 | * | 10/2004 | Cazaux et al. | |

FOREIGN PATENT DOCUMENTS

| AU | 2004200954 | * | 3/2004 |
| WO | WO 03/055465 A1 | * | 7/2003 |

OTHER PUBLICATIONS

Handbook of Pharmaceutical Excipients (Fifth Edition). Edited by Rowe, Sheskey and Owen. Pharmaceutical Press. 2006. pp. 155, 244, 454, 466, 580, 624, 629, 713, 714, 737 and 811.*
Chan, K.P., Goh, K.T., Chong, C.Y., Teo, E.S., Lau, G., and Ling, A.E.; "Epidemic Hand, Foot, and Mouth Disease Caused by Human Enterovirus 71, Singapore;" Emerging Infectious Diseases; vol. 9, No. 1; Jan. 2003; pp. 78-85.
Chan, L.G, et al.; "Deaths of Children During an Outbreak of Hand, Foot, and Mouth Disease in Sarawak, Malaysia; Clinical and Pathological Characteristics of the Disease;" Clinical Infectious Diseases; Feb. 2000; pp. 678-683.
Silverman, S. and Miller, C.S; "Diagnosis and Treatment of Viral Infections;" Oral and Maxillofacial Surgery Clinics; 2003; pp. 79-89.
Chen, K.T, Chang, H.L., Wang, S.T., Cheng, Y.T., and Yang, J.Y.; "Epidemiologic Features of Hand-Foot-Mouth Disease and Herpangina Caused by Enterovirus 71 in Taiwan;" Official Journal of the American Academy of Pediatrics; 2007; pp. 244-253.

* cited by examiner

*Primary Examiner* — Leslie A. Royds Draper
(74) *Attorney, Agent, or Firm* — Perkins Coie LLP; Viola T. Kung

(57) ABSTRACT

A pharmaceutical acceptable composition is provided. The composition comprises an effective amount of a non-steroidal anti-inflammatory drug (NSAID), a local anesthetic, and an antiviral drug.

5 Claims, 3 Drawing Sheets

PHARMACEUTICAL ACCEPTABLE COMPOSITION CONTAINING NON-STEROIDAL ANTI-INFLAMMATORY DRUG AND LOCAL ANESTHETICS

CROSS-REFERENCE TO RELATED APPLICATION

This application claims the priority benefit of provisional application Ser. No. 60/968,654, filed Aug. 29, 2007, and the full disclosure of which is incorporated herein by reference.

BACKGROUND

1. Field of Invention

The present invention relates to a pharmaceutical composition. More particularly, the present invention relates to a pharmaceutical acceptable composition containing a non-steroidal anti-inflammatory drug and a local anesthetic.

2. Description of Related Art

Among the herpes viruses, two commonly known viruses are herpes simplex virus types 1 and 2, referred to as HSV1 and HSV2 and varicella-zoster virus (VZV).

HSV1 causes orofacial lesions, commonly known as fever blisters or cold sores. These lesions most commonly appear on the lips, but may appear on the face, in the mucous membrane lining of the oral cavity, in the eye and nose, and occasionally on the trunk of hands. Infections of the mouth are designated with the term herpes labialis, also called cold sore (feverblister). Other parts of the face can also be affected and the infections thereof are referred to as facial herpes simplex. The infection can also manifest itself on other parts of the body. Approximately 30% of the United States population suffers from recurrent episodes of HSV1.

HSV2, which is less common than HSV1, causes genital lesions. Conversely, genital herpes is caused in about 30% of cases by HSV1.

Varicella-zoster virus (VZV) causes varicella, commonly known as chicken pox, and herpes zoster, commonly known as shingles. Shingles affects the skin and nerves and is characterized by groups of small blisters or lesions appearing along certain nerve segments. The lesions are most often seen on the back and may be preceded by a dull ache in the affected site.

Once an individual has been infected with the herpes virus, the virus will thereafter remain latently in the body. In latent state, the virus is situated in nerve cell bodies in the ganglia. Due to particular stimuli, such as influenza infection, other respiratory disorders, gastrointestinal infections, stress, fatigue, menstruation, pregnancy, allergy, sunlight, or fever, the latent virus can be activated and travel from the ganglia along the well-defined nerve paths to the skin surface and there multiply and cause the symptoms.

There is no treatment known to kill the herpes virus at this time. Most of the available treatments can only help to accelerate the healing of the lesions and the associated symptoms, but have not been shown to be efficacious in the treatment of herpes virus infections.

The best known treatment for herpes virus infections at this time is probably Zovirax® Ointment (Glaxo Wellcome), which contains the active ingredient acyclovir. Acyclovir, 9-(2-hydroxyethoxymethyl), is a purine nucleoside analogue targeting viral encoded DNA polymerase. Other purine nucleoside analogues which are commercially available for treating herpes virus infections include ganciclovir (Roche), penciclovir (Novartis) and foscarnet (Astra). Although effective, these purine nucleoside analogues are poorly soluble in water and demonstrate low bioavailability. These, accompanying the relative long recovery time required (i.e., generally takes longer than 2 weeks for patients to recover).

In the management of pain and discomfort, two kinds of drugs are widely used. The first kind is local anesthetics. Local anesthetics reversibly block the impulse conduction along nerves and other excitable membranes that primarily utilize sodium channels. Clinically, this action blocks the pain sensation from specific areas of the body.

Among the local anesthetics, lidocaine, 2-(diethylamino)-N-(2,6-dimethylphenyl)-acetamide, is particularly known for its treatment of ventricular tachycardia (an arrythmia of the heart) as an intravenous injection solution. (See e.g., U.S. Pat. No. 3,968,205). Lidocaine is also widely used as a vasoconstrictor to reduce regional blood flow in topical applications or aerosols (such as nasal aerosols to reduce nasal congestion). (See eg., U.S. Pat. No. 5,534,242). In addition, lidocaine is known for its therapeutic effects in reducing post-herpetic neuralgia (PHN) nerve injury pain from shingles (herpes zoster and post herpetic neuralgia) and analogous neuropathies. For example, U.S. Pat. No. RE37,727 discloses methods employing lidocaine intradermal administration by transport lidocaine from the skin surface, using patches and dressings, into the skin.

The second kind is non-steroidal anti-inflammatory drug (NSAID). NSAIDs are among the most widely used drugs, probably due to their therapeutic properties as anti-inflammatories, analgesics, anti-pyretics, and anti-thrombolics and are used to treat a variety of clinical conditions manifesting such symptoms as pain, inflammation, fever, and to treat and prevent atherosclerosis.

Among the NSAIDs, diclofenac, which is 2-(2,6-dichloro-anilino)-phenyl-acetic acid, is particularly known for its role as an anti-rheumatic agent for treatment of rheumatoid arthritis. Another NSAID similar to diclofenac and also belongs to the acetic acid class of NSAIDs is ketorolac. Ketorolac, which is 5-benzoyl-2,3-dihydro-1H-pyrrolizine-1-carboxylic acid, is comparable to opioids in terms of providing pain relief. For example, the overall analgesic effect of 30 mg of ketorolac is equivalent to that of 6 to 12 mg of Morphine.

SUMMARY

A method of treating skin of a patient with pain and/or inflammation associated with lesions/blisters by herpes virus or enterovirus is provided. The method comprises the following steps. A topical composition is topically applied to the skin of the patient to decrease at least one of the following: lesion number on the skin, total lesion area on the skin, and the virus titer. The topical composition comprising an effective amount of a non-steroidal anti-inflammatory drug (NSAID), a local anesthetic, and an antiviral drug. The NSAID can be diclofenac or ketorolac. The local anesthetic can be lidocaine. The antiviral drug can be acyclovir, penciclovir, ganciclovir, a prodrug thereof or a mixture thereof. The prodrug of the acyclovir comprises valacyclovir, and the prodrug of the peniclovir comprises famciclovir.

A pharmaceutical acceptable composition is provided. The composition comprises an effective amount of a non-steroidal anti-inflammatory drug (NSAID), a local anesthetic, and an antiviral drug. The NSAID can be diclofenac or ketorolac. The local anesthetic can be lidocaine. The antiviral drug can be acyclovir, penciclovir, ganciclovir, a prodrug thereof or a mixture thereof. The prodrug of the acyclovir comprises valacyclovir, and the prodrug of the peniclovir comprises famciclovir.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows.

DETAILED DESCRIPTION

Figure 1:
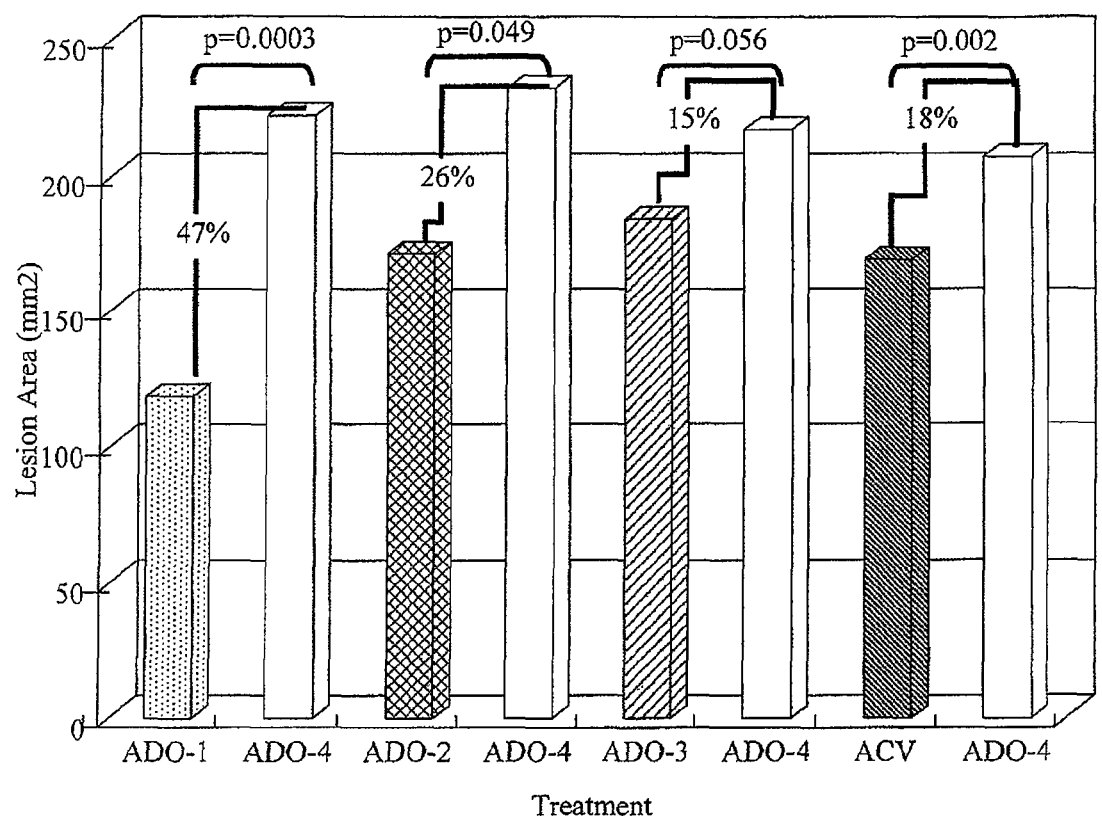
FIGS. 1-3 show analysis results of the animal test with the level of significance of $p \leq 0.05$ for the experiments.

A novel pharmaceutical acceptable composition is provided. The composition comprises an effective amount of a non-steroidal anti-inflammatory drug (NSAID), a local anesthetic, and an antiviral drug. The NSAID can be diclofenac or ketorolac. The local anesthetic can be lidocaine. The antiviral drug can be acyclovir, peniclovir, ganciclovir, a prodrug thereof or a mixture thereof. The prodrug of the acyclovir comprises valacyclovir, and the prodrug of the peniclovir comprises famciclovir.

According to an embodiment of this invention, the effective amount of the NSAID, the local anesthetic, or the antiviral drug can be 0.1-20 wt %. According to another embodiment, the effective amount of the NSAID, the local anesthetic, or the antiviral drug can be 0.1-15 wt %. According to yet another embodiment, the effective amount of the NSAID, the local anesthetic, or the antiviral drug can be 0.5-15 wt %. According to yet another embodiment, the effective amount of the NSAID, the local anesthetic, or the antiviral drug can be 0.1-10 wt %. According to yet another embodiment, the effective amount of the NSAID, the local anesthetic, or the antiviral drug can be 0.5-10 wt %. According to yet another embodiment, the effective amount of the NSAID, the local anesthetic, or the antiviral drug can be 1-5 wt %.

Some preparation examples (gel or cream formulation) of the pharmaceutical acceptable composition described above are disclosed below. These examples are illustrative, but not limiting the scope of the present invention. Reasonable variations, such as those occur to reasonable artisan, can be made herein without departing from the scope of the present invention.

EXAMPLES 1-6

Preparation of Gel Containing Diclofenac Acid Lidocaine Salt and Acyclovir

A gel containing diclofenac acid lidocaine salt named as lidofenac and acyclovir for topical treatment of pain and/or inflammation caused by HSV and/or VZV infection was prepared by the following step:

1. Carbopol (carboxypolymethylene) was mixed with a proper amount of isopropyl alcohol. Then, purified water was added to the mixture and mixed well to form a first homogeneous solution.
2. Diclofenac acid lidocaine salt, acyclovir, propylene glycol, and isopropyl alcohol were mixed together to form a second homogeneous solution.
3. L-menthol was added to isopropyl alcohol and mixed to form a third homogeneous solution.
4. The second and the third homogeneous solution were added to the first homogeneous solution to form a uniform mixture. Then, triethanolamine was added to the mixture and mixed well to obtain a topical formulation in a form of a gel.

Some preparation examples (Examples 1-6) are listed by example in Table 1 below. In Table 1, the gel contains 0.1 wt % to 20 wt % of diclofenac acid lidocaine salt and 0.1 wt % to 20 wt % of acyclovir.

TABLE 1

| | Examples | | | | | |
|---|---|---|---|---|---|---|
| | 1 | 2 | 3 | 4 | 5 | 6 |
| First homogeneous solution | | | | | | |
| Carbopol | 15 g | 15 g | 15 g | 17 g | 15 g | 15 g |
| Isopropyl Alcohol | 150 g | 50 g | 200 g | 50 g | 100 g | 50 g |
| Purified Water | 405 g | 205 g | 503 g | 402 g | 354 g | 409 g |
| Second homogenous solution | | | | | | |
| Diclofenac Acid Lidocaine Salt | 50 g | 200 g | 1 g | 200 g | 1 g | 5 g |
| Acyclovir | 50 g | 200 g | 1 g | 1 g | 200 g | 100 g |
| Propylene Glycol | 200 g | 200 g | 200 g | 200 g | 200 g | 300 g |
| Isopropyl Alcohol | 50 g | 50 g | 50 g | 50 g | 50 g | 50 g |
| Third homogeneous solution | | | | | | |
| L-Menthol | 10 g | 10 g | 10 g | 10 g | 10 g | 1 g |
| Isopropyl Alcohol | 250 g | 50 g | 50 g | 50 g | 50 g | 50 g |
| | | Final added | | | | |
| Triethanolamine | 20 g | 20 g | 20 g | 20 g | 20 g | 20 g |
| Total Weight | 1000 g | 1000 g | 1000 g | 1000 g | 1000 g | 1000 g |

EXAMPLES 7-12

Preparation of Cream Containing Diclofenac Acid Lidocaine Salt and Acyclovir

A cream containing diclofenac acid lidocaine salt and acyclovir for topical treatment of pain and/or inflammation caused by HSV and/or VZV infection was prepared by the following step:

1. Preparation of the oil phase: A first mixing vessel was submerged in a hot water bath (80±2° C.). Acyclovir, methyl paraben, propyl paraben, cetyl alcohol, sorbitan monostearate 60, spermaceti synthetic, and miglyol 812 were added into the first mixing vessel and stirred to mix well. Stearic acid, and dimethyl polysiloxane are additionally added into the first mixing vessel, too (see Table 2). The mixture was filtered by a number 150 mesh one time to remove particles.

2. Preparation of the water phase: A second mixing vessel was submerged in a hot water bath (80±2° C.). Diclofenac acid lidocaine salt, polysorbate 60, propylene glycol, and purified water were added into the second mixing vessel and stirred to complete dissolve. Sodium citrate was additional added into the second mixing vessel, too (see Table 2). The mixture was filtered by a number 150 mesh one time to remove particles.

3. Emulsification: The oil phase was transferred into a steam-jacketed tank having a vacuum pressure of 35-40 cmHg. The water phase was added slowly in to the steam-jacketed tank at a constant stirring speed by using a Homo-Mixer (25-35 Hz) for 25 minutes.

4. The emulsion of the previous step was cooled to a temperature of 30° C. under a slowly stirred condition to obtain a topical formulation in a dosage form of a cream.

Some preparation examples (Examples 7-12) are listed by example in Table 2 below. In Table 2, the cream contains 0.1 wt % to 20 wt % of diclofenac acid lidocaine salt and 0.1 wt % to 20 wt % of acyclovir. In addition, since the physical and chemical properties of penciclovir and ganciclovir are similar to acyclovir, the acyclovir in Table 2 can be easily replaced by penciclovir and ganciclovir.

The prodrug of the acyclovir comprises valacyclovir, and the prodrug of the penciclovir comprises famciclovir.

Some animal tests of the method described above are disclosed below. These examples are illustrative, but not limiting the scope of the present invention. Reasonable variations, such as those occur to reasonable artisan, can be made herein without departing from the scope of the present invention.

The compounds tested in this section are listed in Table 3. The tested animals were Hartley outbred albino guinea pigs.

TABLE 3

| Example | Codes | Acyclovir | Diclofenac acid lidocaine salt | Vehicle | amount |
|---|---|---|---|---|---|
| 13 | ADO-1 | 5 wt % | 5 wt % | ADO-4* | 250 mg |
| 14 | ADO-2 | 5 wt % | — | ADO-4 | 250 mg |
| 15 | ADO-3 | — | 5 wt % | ADO-4 | 250 mg |
| 16 | ACV** | 5 wt % | — | PEG | 250 mg |

*The composition of ADO-4 was the composition of example 7 without adding the active drug, i.e. acyclovir and diclofenac acid lidocaine salt
**ACV is a commercial product, Zovirax ® Ointment of Glaxo Wellcome, and was used as a positive control.

HSV-1 virus stock was applied to skin on back of each guinea pig. The day of inoculation was Day 0. Approximately 250 mg of drug or vehicle was applied to each site for 4 times per day on Days 1, 2, and 3.

On Day 4, lesions were counted from the animals, and pictures of the animals taken were used later to measure

TABLE 2

|  | Example | | | | | |
|---|---|---|---|---|---|---|
|  | 7 | 8 | 9 | 10 | 11 | 12 |
| Oil Phase | | | | | | |
| Acyclovir | 50 g | 200 g | 1 g | 1 g | 200 g | 100 g |
| Methyl Paraben | 1 g | 1 g | 1 g | 1 g | 1 g | 1 g |
| Propyl Paraben | 1 g | 1 g | 1 g | 1 g | 1 g | 1 g |
| Cetyl Alcohol | 60 g | 50 g | 60 g | 50 g | 60 g | 50 g |
| Sorbitan monostearate 60 | 12 g | 12 g | 12 g | 12 g | 12 g | 12 g |
| Stearic acid | 20 g | — | 20 g | — | 20 g | 50 g |
| Spermaceti Synthetic | 50 g | 30 g | 50 g | 30 g | 50 g | 30 g |
| Dimethyl Polysiloxane | 30 g | — | 30 g | — | 30 g | — |
| Miglyol 812 | 70 g | 70 g | 70 g | 70 g | 70 g | 170 g |
| Water Phase | | | | | | |
| Diclofenac Acid Lidocaine Salt | 50 g | 200 g | 1 g | 200 g | 1 g | 5 g |
| Polysorbate 60 | 36 g | 36 g | 36 g | 45 g | 36 g | 36 g |
| Propylene Glycol | 160 g | 60 g | 160 g | 60 g | 160 g | 60 g |
| Sodium citrate | 10 g | — | 10 g | — | 10 g | — |
| Purified water | 450 g | 340 g | 548 g | 530 g | 450 g | 485 g |
| Total Weight | 1000 g | 1000 g | 1000 g | 1000 g | 1000 g | 1000 g |

EXAMPLES 13-16

Animal Test

A method of treating skin of a patient with pain and/or inflammation associated with lesions/blisters by herpes virus or enterovirus is provided. The method comprises the following steps. A topical composition is topically applied to the skin of the patient to decrease at least one of the following: lesion number on the skin, total lesion area on the skin, and the virus titer. The topical composition comprising an effective amount of a non-steroidal anti-inflammatory drug (NSAID), a local anesthetic, and an antiviral drug. The NSAID can be diclofenac or ketorolac. The local anesthetic can be lidocaine. The antiviral drug can be acyclovir, penciclovir, ganciclovir, a prodrug thereof or a mixture thereof.

lesion sizes. The animals were sacrificed, and full-thickness skin from the different areas was removed and homogenized. Debris was precipitated by centrifugation, and the collected supernatants were frozen at −70° C. until assay for infectivity by plaque formation in VERO 76 cells (Kidneym, African green monkey, ATCC CRL#1587).

Figure 2:
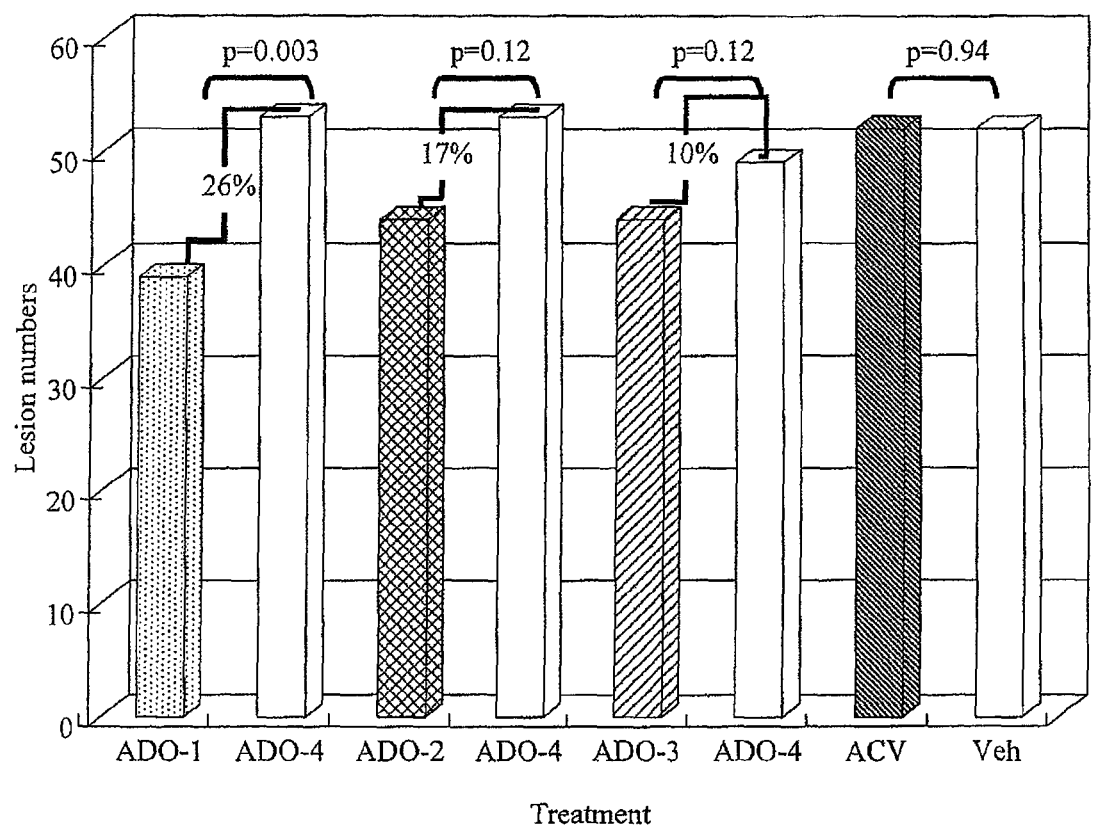
Figure 3:
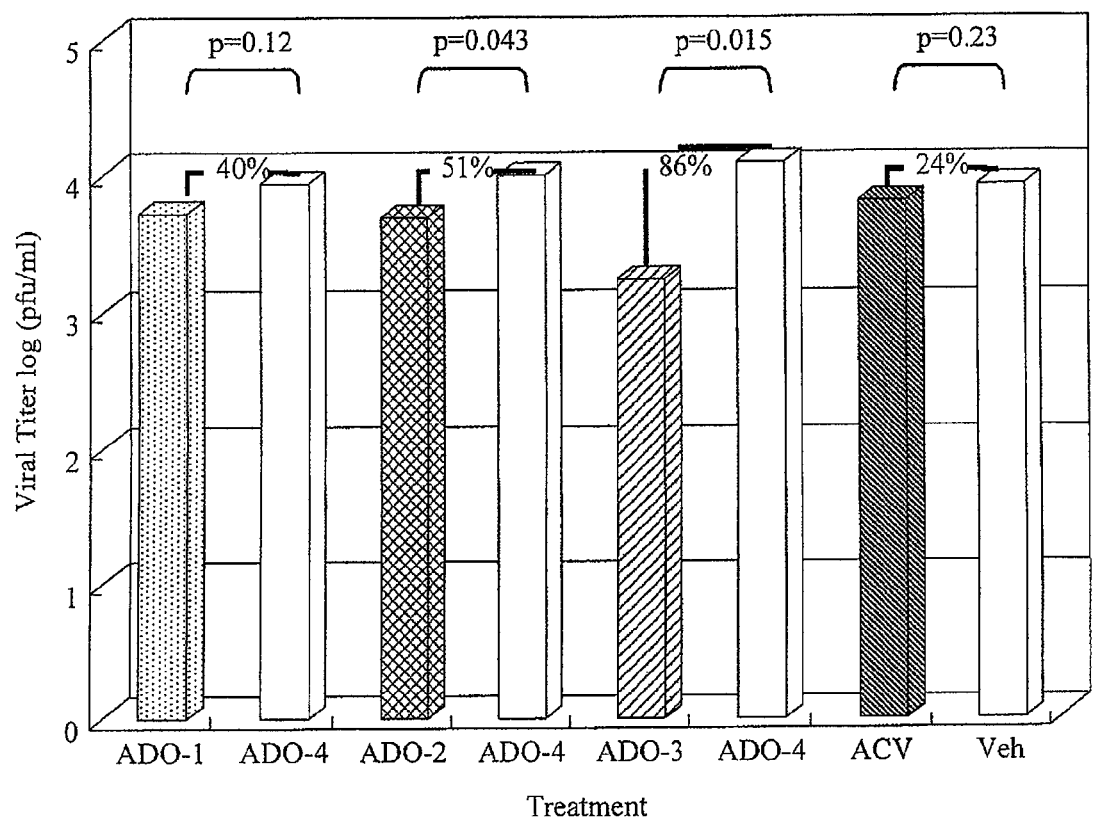

FIGS. 1-3 show analysis results of the animal test with the level of significance of $p \leq 0.05$ for the experiments.

In FIG. 1, ADO-1 (Example 13) achieved statistically significant reductions in lesion area (47%), which has the most distinct reduction effect when compared to ADO-2 (26%, Example 14), ADO-3 (15%, Example 15), and ACV (18%, Example 16).

In FIG. 2, ADO-1 (Example 13) also achieved statistically significant reductions in lesion number (26%), which has the most distinct reduction effect when compared to ADO-2 (17%, Example 14), ADO-3 (10%, Example 15), and ACV (Example 16).

In FIG. 3, it was surprised that ADO-3 (Example 15), which did not contain any antiviral drug, has the most distinct reduction effect (86%) in viral titer when compared to ADO-1 (40%, Example 13), ADO-2 (51%, Example 14), and ACV (24%, Example 16).

In addition, compounds that are well-tolerated in humans can often be irritating to the tested animals, so that dermal irritation here may not be a predictor of dermal irritation in humans.

Accordingly, a method and a pharmaceutically acceptable composition of treating skin of a patient with pain and/or inflammation associated with lesions/blisters by herpes virus have been provided. The treatment method and the pharmaceutically acceptable composition not only can be applied to the lesions/blisters caused by herpes virus, but also can be applied to the lesions/blisters caused by enterovirus, since enterovirus usually cause symptoms, such as enterovirus usually cause wheals, papules, blister, ulcer, which are similar to those of herpes virus. Please see the following references, which are incorporated entirely herein by reference.

1. Epidemiological Features Of Hand-Foot-Mouth Diseases And Herpangina Caused By Enterovirus 71 In Taiwan, 1998 2005 (Kow-Tong Chen et al., American Academy of Pediatrics, Vol. 120, 2008, pp e243-e252).

2. Deaths of Children during an Outbreak of Hand, Foot, and Mouth Disease in Sarawak, Malaysia: Clinical and Pathological Characteristics of the Disease (L. G. Chan et al., Clinical Infectious Disease Vol. 31, 2000, pp 678-683).

3. Diagnosis and treatment of viral infections (Sol Silverman, Jr. et al. Oral and Maxillofacial Surgery Clinics, Vol. 15, 2003, pp 79-89).

4. Epidemic Hand, Foot and Mouth Disease Caused by Human Enterovirus 71, Singapore (Kwai Peng Chan et al. Emerging Infectious Disease, Vol. 9, 2003, pp 78-85).

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A pharmaceutical composition comprising 5% (by weight) of diclofenac acid lidocaine salt and 5% (by weight) of acyclovir.

2. The pharmaceutical composition according to claim 1, further comprising methyl paraben, propyl paraben, cetyl alcohol, sorbitan monostearate, stearic acid, spermaceti, dimethyl polysiloxane, caprylic/capric triglyceride, polysorbate, propylene glycol, and water.

3. A method of reducing the total lesion area and reducing the lesion number on the skin of a patient afflicted with lesions caused by herpes virus, comprising:
  topically applying a topical composition to the skin of the patient, wherein the topical composition comprises 5% (by weight) of diclofenac acid lidocaine salt and 5% (by weight) of acyclovir.

4. The method of claim 3, wherein the herpes virus is herpes simplex virus or herpes zoster virus.

5. The method of claim 3, wherein the topical composition further comprises methyl paraben, propyl paraben, cetyl alcohol, sorbitan monostearate, stearic acid, spermaceti, dimethyl polysiloxane, caprylic/capric triglyceride, polysorbate, propylene glycol, and water.

* * * * *